US00PP29326P2

(12) United States Plant Patent
Lambalk

(10) Patent No.: US PP29,326 P2
(45) Date of Patent: May 29, 2018

(54) ***HIBISCUS* PLANT NAMED 'SUMMER HOLIDAY'**

(50) Latin Name: *Hibiscus syriacus*
Varietal Denomination: SUMMER HOLIDAY

(71) Applicant: Johannes Jacobus Maria Lambalk, Middenbeemster (NL)

(72) Inventor: Johannes Jacobus Maria Lambalk, Middenbeemster (NL)

(73) Assignee: Valkplant BV (NL)

( * ) Notice: Subject to any disclaimer, the term of this patent is extended or adjusted under 35 U.S.C. 154(b) by 0 days. days.

(21) Appl. No.: 15/530,764

(22) Filed: Feb. 24, 2017

(51) Int. Cl.
*A01H 5/02* (2018.01)

(52) U.S. Cl.
USPC ..... Plt./257
CPC ..... *A01H 5/02* (2013.01)

(58) Field of Classification Search
USPC ..... Plt./257
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Hibiscus* cultivar named 'SUMMER HOLIDAY' is disclosed, characterized by fully double white to light pink flowers with a red-purple eye. Plants are compact and have flowers that will open in cold climates. The new variety is a *Hibiscus*, normally produced as an outdoor garden or container plant.

1 Drawing Sheet

Latin name of the genus and species: *Hibiscus syriacus*. Variety denomination: 'SUMMER HOLIDAY'.

BACKGROUND OF THE INVENTION

The new *Hibiscus* cultivar is a product of a planned breeding program conducted by the inventor in Middenbeemster The Netherlands. The objective of the breeding program was to produce new *Hibiscus syriacus* varieties with double flowers on dwarf plants. The self-pollination resulting in this new variety was made during 1997.

The parent is the unpatented *Hibiscus syriacus* 'Leopoldii', which the inventor used in a self-pollination breeding program. The new variety was identified as a potentially interesting selection during 2000. Selection was made at a research nursery in Middenbeemster, The Netherlands.

Asexual reproduction of the new cultivar 'SUMMER HOLIDAY' was first performed in February 2014 at a commercial nursery in Hazerswoude, The Netherlands. Vegetative soft wood cuttings were grafted onto an unnamed, unpatented *Hibiscus syriacus* rootstock. Subsequent propagation has shown that the unique features of this cultivar are stable and reproduced true to type in 6 successive generations.

SUMMARY OF THE INVENTION

The cultivar 'SUMMER HOLIDAY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUMMER HOLIDAY' These characteristics in combination distinguish 'SUMMER HOLIDAY' as a new and distinct *Hibiscus* cultivar:

1. Double, white to light pink with a red-purple eye flowers
2. Flowers will open in cold climates.
3. Compact plants.

PARENT COMPARISON

Plants of the new cultivar 'SUMMER HOLIDAY' are similar to plants of the parent variety in most horticultural characteristics, however, plants of the new cultivar 'SUMMER HOLIDAY' differ in the following;

1. The new variety has white to light pink with a red-purple eye flowers, flowers of the parent variety are medium pink.
2. The new variety has a double flower, the parent variety has a semi-double flower.

COMMERCIAL COMPARISON

Plants of the new cultivar 'SUMMER HOLIDAY' can be compared to the variety *Hibiscus* 'Notwoodtwo', U.S. Plant Pat. No. 12,612. These varieties are similar in most horticultural characteristics however, 'SUMMER HOLIDAY' differs in the following:

1. Flower color of the new variety is white to light pink, with a red-purple eye. Flower color of this comparator is all white, with no pink coloration and no eye.

BRIEF DESCRIPTION OF THE PHOTOGRAPH

The accompanying photograph illustrates in full color a typical flower of 'SUMMER HOLIDAY'. Age of the plant photographed is approximately 1 year. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, 6th edition, except where general terms of ordinary dictionary significance are used. The following observations and measurements describe 'Summer Holiday' plants grown in a polyhouse in Grand Haven, Mich. Measurements were taken during July of 2015. The plants were 2 years old in 3 gallon containers. The growing temperature ranged from approximately 18° C. to 27° C. during the day and 5° C. to 10° C. at night. Measurements and numerical values represent averages of typical plant types.

Botanical classification: *Hibiscus syriacus* 'SUMMER HOLIDAY'.

PROPAGATION

Time to initiate roots: 20 days at approximately 25° C.

Root description: Fibrous, medium root thickness. Tan/brown in color, not effectively measured with a color chart.

Time to produce a rooted young plant: About 90 days at 25° C.

PLANT

Plant type: Perennial shrub.

Age of plant described: Approximately 2 years old.

Growth habit: Upright.

Pot size of plant described: 3 gallon pot.

Overall plant shape: Upright, broad ovate.

Height: 59 cm.

Plant spread: 58.5 cm

Plant vigor: Moderate.

Branching characteristics: No basal branching. Very upright plant with branches at acute angles.

Length of primary lateral branches: Average range 5 to 25 cm.

Diameter of lateral branches: 3 mm.

Quantity of lateral branches: Average 25.

Stem:

*Stem shape.*—Round.

*Stem strength.*—Strong.

*Color.*—Stem: Near RHS Greyed-Brown 199C.

*Texture.*—Glabrous.

*Angle of attachment.*—Branches very upright, occurring at acute angles from center of plant.

Internode length: 4 cm on average.

FOLIAGE

Leaf:

*Arrangement.*—Alternate, single.

*Leaf shape.*—Rhomboid, lobed.

*Average length.*—6 cm.

*Average width.*—4 cm.

*Apex.*—Acute.

*Base.*—Cuneate.

*Margin.*—Undulate, irregular and infrequent serrations.

*Texture of top surface.*—Smooth with distinct veins.

*Texture of bottom surface.*—Scabrose with raised veins.

*Color.*—Young foliage upper side: Near RHS Green 139A. Young foliage under side: Near RHS Green 137B. Mature foliage upper side: Near RHS Green 139A. Mature foliage under side: Near RHS Yellow-Green 144A.

*Venation.*—Pattern: Palmate. Color upper side: Near RHS Green 138B. Color under side: Near RHS Yellow-Green 144D.

*Petiole.*—Average Length: 1 cm. Diameter: 1.5 mm. Petiole color upper side: Near RHS Green 143C. Petiole color lower side: Near RHS Green 141B. Petiole Texture upper side: Pubescent. Petiole Texture lower side: Smooth.

FLOWER

Natural flowering season: Spring through Summer continuously.

Flowering form: Fully double, whorled.

Flower habit: Solitary, emerging from leaf axils.

Flower longevity on plant: About 4 days.

Quantity of flowers per plant: About 50 flowers and buds on a mature plant in full bloom.

Flower shape: Overall shape is a half dome.

Flower aspect: Upright and slightly outward.

Size:

*Length.*—3.5 cm.

*Diameter.*—8 cm.

Flower other characteristics:

*Persistence.*—Self-cleaning.

*Fragrance.*—Herbaceous.

Bud:

*Shape.*—Ovate.

*Length.*—Average 2.0 cm.

*Diameter.*—Average 1.0 cm.

*Color.*—Near Red 38A.

Petal:

*Petal arrangement.*—Whorled and a thick central whorl of petaloids.

*Number of petals per flower.*—5 large outer petals.

*Fused.*—No.

*Petal shape.*—Obovate.

*Petal base.*—Truncate.

*Margin.*—Entire, undulate.

*Tip shape.*—Obovate.

*Length.*—3.75 cm.

*Width.*—4 cm.

*Texture.*—Upper: Glabrous. Lower: Glabrous.

*Appearance.*—Upper surface matte with glossy base. Lower surface matte.

Petal color:

*When opening.*—Upper surface: Near Red-Purple 69C. Lower surface: Near Red-Purple 69C.

*Fully opened.*—Upper surface: Near Red-Purple 69C. Basal blotch, "eye" near Red-Purple 59B. Towards margin, color turns near White N155B. Lower surface: Near Red-Purple 69C. Basal blotch, "eye" near Red-Purple 59C. Towards margin, color turns near White N155B.

*Fading to.*—Upper surface: Near RHS Red-Purple 69C, with large areas White N155B. Basal blotch, "eye" near Red-Purple 59C. Lower surface: Near RHS Red-Purple 69C, with large areas White N155B. Basal blotch, "eye" near Red-Purple 59C.

Petaloids:

*Arrangement.*—Thick central whorl of petaloids at the base of the style and along the style.

*Number of petaloids per flower*.—Average 18.
*Shape*.—Irregular orbicular or obovate.
*Base*.—Truncate.
*Margin*.—Entire.
*Tip shape*.—Obtuse to broadly acute, irregularly lobed.
*Length*.—Average 2.75 cm.
*Width*.—Average range 1 to 2.5 cm.
*Texture*.—Upper: Glabrous. Lower: Glabrous.
*Appearance*.—Upper surface matte with glossy base. Lower surface matte.

Petaloid color:
*When opening*.—Upper surface: Near Red-Purple 69C. Basal blotch, "eye" near Red-Purple 59B. Lower surface: Near Red-Purple 69C. Basal blotch, "eye" near Red-Purple 59B.
*Fully opened*.—Upper surface: Near Red-Purple 69C. Basal blotch, "eye" near Red-Purple 59B. Lower surface: Near Red-Purple 69C. Basal blotch, "eye" near Red-Purple 59B.

Epicalyx:
*Shape*.—Radial.
*Length*.—1.7 cm.
*Diameter*.—2 cm.
*Epicalyx sepals*.—Arrangement: Rotate. Number: Average 8. Shape: Linear. Tip: Acicular. Base: Truncate. Margin: Entire. Length: 1.0 cm. Width: 2 mm. Texture, Upper: Rough; slightly pubescent. Texture, Lower: Smooth. Color: Upper surface: Yellow-Green 144B. Under surface: Near Green 141B.

Calyx:
*Shape*.—Rotate.
*Length*.—1.7 cm.
*Diameter*.—2 cm.

Sepal:
*Arrangement*.—Rotate.
*Number*.—Average 4 to 5.
*Shape*.—Deltate.
*Tip*.—Acute.
*Base*.—Truncate.
*Margin*.—Entire.
*Length*.—7 mm.
*Width*.—1 cm.
*Texture, upper*.—Rough; slightly pubescent.
*Texture, lower*.—Smooth.
*Color*.—Upper surface: Near Green 141D. Under surface Near Yellow-Green 144C.

Peduncle:
*Length*.—2 to 5 cm.
*Diameter*.—2.5 mm.
*Color*.—Near RHS Yellow-Green 144B.
*Orientation*.—Straight.
*Strength*.—Strong.
*Texture*.—Softly pubescent.

REPRODUCTIVE ORGANS

Stamens:
*Number*.—Average 16, clustered and implanted in style, typical of *Hibiscus*.
*Filament length*.—7 mm.
*Filament color*.—Near Green-White 157D.

Anthers:
*Shape*.—Dorsifixed.
*Length*.—2 mm.
*Color*.—Near Green-White 157D.
*Pollen color*.—Near Green-White 157D.
*Pollen amount*.—Moderate.

Pistil:
*Number*.—6.
*Length*.—1.0 cm.
*Style*.—Length: 1.7 cm. Color: Near Green-White 157D.
*Stigma*.—Shape: Peltate. Color: Near Green-White 157D.
*Ovary color*.—Near RHS Yellow-Green 150C.

OTHER CHARACTERISTICS

Seeds and fruits: Not observed to date.
Disease/pest resistance: Neither resistance nor susceptibility to normal diseases and pests of *Hibiscus syriacus* have been observed.
Garden performance: Good tolerance, performs well in humid conditions.
Temperature tolerance: Low temperature tolerance to at least USDA zone 4, high temperature tolerance to at least 40° C.

What is claimed is:

1. A new and distinct cultivar of *Hibiscus* plant named 'SUMMER HOLIDAY' as herein illustrated and described.

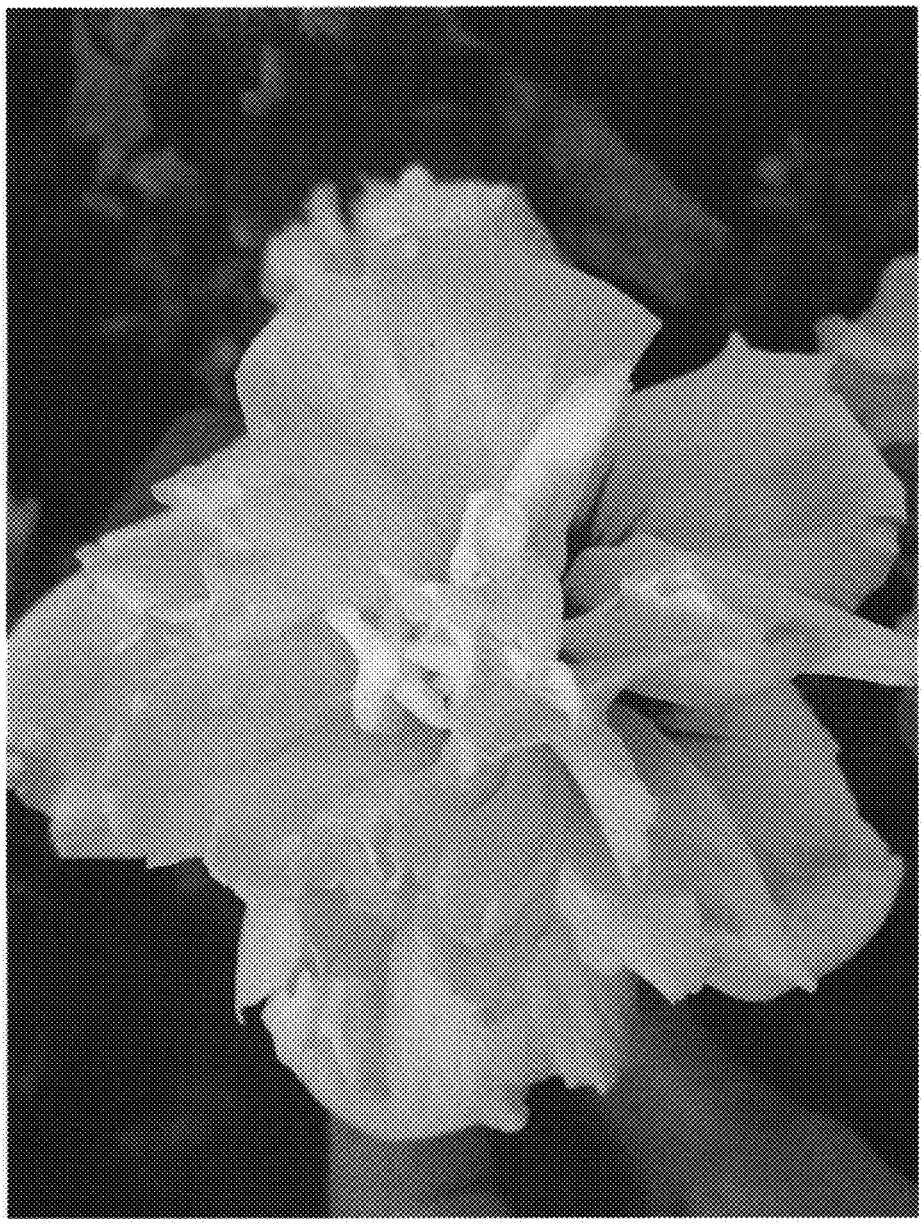

* * * * *